US006544178B1

(12) United States Patent
Grenon et al.

(10) Patent No.: US 6,544,178 B1
(45) Date of Patent: Apr. 8, 2003

(54) METHODS AND SYSTEMS FOR VOLUME RENDERING USING ULTRASOUND DATA

(75) Inventors: Stephen Michael Grenon, Hillsborough, NC (US); Paul J. Hilts, Durham, NC (US); Richard Holloway, Chapel Hill, NC (US)

(73) Assignees: Volumetrics Medical Imaging, Durham, NC (US); Duke University, Durham, NC (US)

( * ) Notice: Subject to any disclaimer, the term of this patent is extended or adjusted under 35 U.S.C. 154(b) by 28 days.

(21) Appl. No.: 09/707,241

(22) Filed: Nov. 6, 2000

Related U.S. Application Data

(60) Provisional application No. 60/163,856, filed on Nov. 5, 1999.

(51) Int. Cl.$^7$ ................................................. A61B 8/00
(52) U.S. Cl. ....................................... 600/443; 128/916
(58) Field of Search .......................... 600/407, 409, 600/410, 424, 427, 437, 443, 439, 447, 461, 471

(56) References Cited

U.S. PATENT DOCUMENTS

| | | | |
|---|---|---|---|
| 4,694,434 A | 9/1987 | von Ramm et al. ............. 367/7 |
| 4,827,413 A | 5/1989 | Baldwin et al. ........ 364/413.19 |
| 4,835,712 A | 5/1989 | Drebin et al. ................ 364/518 |
| 4,984,157 A | 1/1991 | Cline et al. ............. 364/413.13 |
| 4,985,856 A | 1/1991 | Kaufman et al. ............ 364/522 |
| 5,038,302 A | 8/1991 | Kaufman ..................... 364/522 |
| 5,101,475 A | 3/1992 | Kaufman et al. ............ 395/124 |
| 5,261,404 A | * 11/1993 | Mick et al. .................. 128/916 |
| 5,313,567 A | 5/1994 | Civanlar et al. ............. 395/124 |
| 5,546,807 A | 8/1996 | Oxaal et al. .................... 73/606 |
| 5,572,999 A | * 11/1996 | Funda et al. ................. 600/461 |
| 5,588,432 A | * 12/1996 | Crowley ...................... 600/439 |
| 5,594,842 A | 1/1997 | Kaufman et al. ............ 395/124 |
| 5,760,781 A | 6/1998 | Kaufman et al. ............ 345/424 |
| 5,797,849 A | * 8/1998 | Vesely et al. ................ 600/461 |
| 5,810,008 A | * 9/1998 | Dekel et al. ................. 128/916 |
| 6,048,312 A | * 4/2000 | Ishrak et al. ................ 600/443 |
| 6,120,453 A | * 9/2000 | Sharp .......................... 600/463 |
| 6,146,329 A | * 11/2000 | Hayakawa ................... 600/443 |
| 6,167,296 A | * 12/2000 | Shahidi ....................... 600/427 |
| 6,174,285 B1 | * 1/2001 | Clark .......................... 600/443 |
| 6,126,029 A1 | * 4/2001 | Paltieli ........................ 600/427 |
| 6,226,543 B1 | * 5/2001 | Gilboa et al. ............... 600/407 |
| 6,256,529 B1 | * 7/2001 | Holupka et al. ............. 600/439 |
| 6,336,899 B1 | * 1/2002 | Yamazaki .................... 600/443 |
| 6,351,573 B1 | * 2/2002 | Schneider ................... 382/294 |
| 6,423,002 B1 | * 7/2002 | Hossack ...................... 600/439 |

OTHER PUBLICATIONS

Pfister et al.; Entitled: *The VolumePro Real–Time Ray–Casting System*; Mitsubishi Electric, International Conference on Computer Graphics and Interactive Techniques; Proceedings of the SIGGRAPH 1999 Annual Conference on Computer Graphics; Aug. 8–13, 1999, Los Angeles, CA, USA, 10 pages.
www.3dechotech.com; printed May 29, 2001; 3 pages.
www.tomtec.de; printed May 29, 2001; 7 pages.

* cited by examiner

*Primary Examiner*—Francis J. Jaworski
(74) *Attorney, Agent, or Firm*—Myers Bigel Sibley & Sajovec

(57) ABSTRACT

An ultrasound scanner may display volume renderings of objects in real time. In particular, the system can scan an object at a first time using the ultrasound scanner to provide a first 3D ultrasound dataset that represents the object and of an instrument at a first position. A volume rendering of at least a portion of the object and instrument can be displayed. The first position of the instrument can be adjusted relative to the object based on the displayed volume rendering to provide a second position of the instrument. The object is scanned at a second time using the ultrasound scanner to provide a second 3D ultrasound dataset that represents at least a portion of the object and the instrument at the second position.

12 Claims, 9 Drawing Sheets

METHODS AND SYSTEMS FOR VOLUME RENDERING USING ULTRASOUND DATA

CROSS-REFERENCE TO RELATED APPLICATION

This application claims the benefit of U.S. Provisional Patent Application No. 60/163,856, filed Nov. 5, 1999, entitled Real time Volume Rendering of 3-D Ultrasonic Datasets Acquired in Real Time, the entire disclosure of which is incorporated herein by reference.

FIELD OF THE INVENTION

The present invention relates to the field of imaging in general and, more particularly, to ultrasound imaging.

BACKGROUND OF THE INVENTION

Studies of tissues may be assisted by the display of ultrasound data. For example, conventional systems may display ultrasound data acquired in two dimensions (2D), such as B-mode slices. A physician may view the acquired 2D ultrasound data to assist, for example, in guiding a catheter through a patient's body. The 2-D datasets can be acquired using, for example, ultrasound or fluoroscopy imaging techniques. Unfortunately, fluoroscopy may subject the patient to potentially harmful levels of radiation.

An understanding of a given anatomy may also be gained by reviewing images generated from ultrasound data that was acquired beforehand. For example, the ultrasound data may be acquired by a technician and reviewed by a physician after the ultrasound scan is over.

SUMMARY OF THE INVENTION

Figure 1:
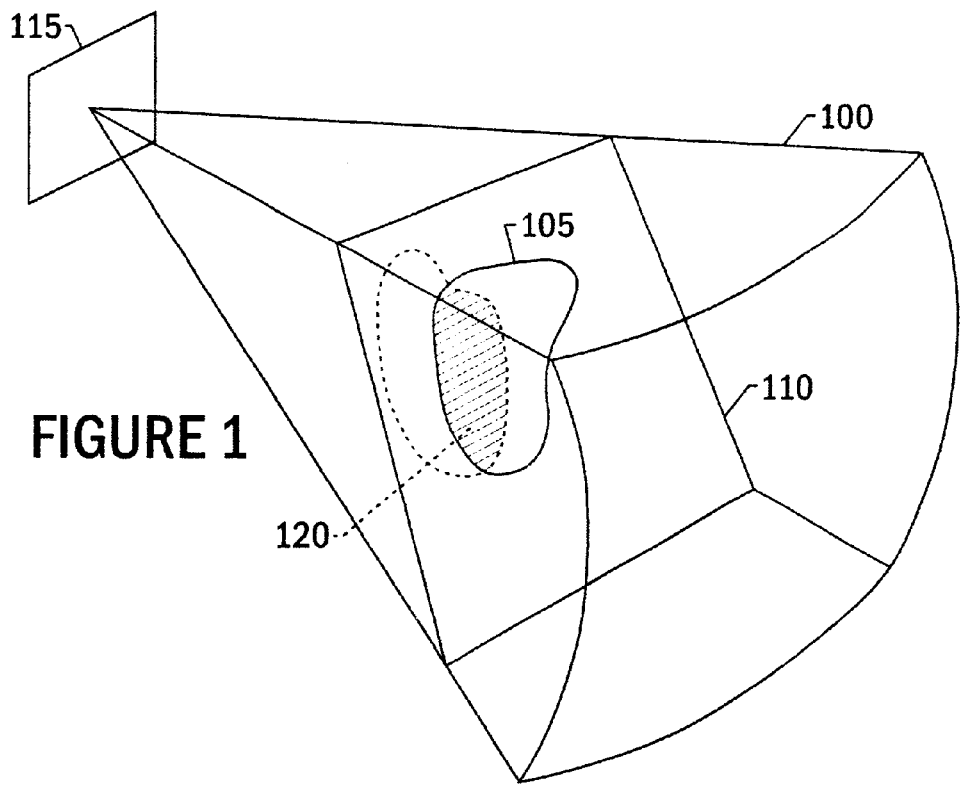
FIG. 1 is a schematic diagram that illustrates scanning of volumes including objects to be studied.

Embodiments according to the present invention can provide methods and systems for volume renderings using ultrasound data. Pursuant to these embodiments, an object can be scanned at a first time using the ultrasound scanner to provide a first 3D ultrasound dataset that represents the object and of an instrument at a first position. A volume rendering of at least a portion of the object and instrument can be displayed. The first position of the instrument can be adjusted relative to the object based on the displayed volume rendering to provide a second position of the instrument. The object is scanned at a second time using the ultrasound scanner to provide a second 3D ultrasound dataset that represents at least a portion of the object and the instrument at the second position.

The adjusted position of the instrument may be seen in a display of a volume rendering of the object and the instrument using the second 3D ultrasound dataset. Moreover, the instrument can be continually guided by repeatedly scanning and displaying the volume renderings of the object and the instrument as the instrument is manipulated. For example, in some embodiments, the instrument can be a catheter used, for example, during examinations of the heart. In such procedures, the instrument may be guided to the heart by reference to features within the rendered volume.

Pursuant to other embodiments of the present invention, ultrasound images can be generated using an ultrasound scanner by scanning an object at a first time with the ultrasound scanner where a scanning parameter is set to a first value to provide a first 3D ultrasound dataset that represents the object at the first time. A volume rendering of at least a portion of the object can be displayed. The first value can be adjusted based on a view that is generated from the first 3D ultrasound dataset. The object can be scanned at a second time with the ultrasound scanner where the scanning parameter is set to a second value to provide a second 3D ultrasound dataset that represents the object at the second time.

Accordingly, the value of the scanning parameter can be adjusted as the object is being scanned by the ultrasound scanner. For example in some embodiments, the scanning parameter can be a position of a transducer used to scan the object. In other embodiments, the scanning parameter can be a scanning gain that can affect the signals that are used to scan the object. In still other embodiments, the scanning parameter can be a depth of scanning that can control how the object is scanned.

Pursuant to additional embodiments, volume renderings of colorflow Doppler ultrasound images can be provided by scanning tissue at a first time using the ultrasound scanner having a scanning parameter set to a first value to provide a first 3D ultrasound dataset that represents the tissue at the first time. A first volume rendering of 3D colorflow Doppler data associated with at least a portion of the tissue can be displayed based on the first 3D ultrasound dataset. The first value can be adjusted based on the first volume rendering. The tissue can be scanned at a second time using the ultrasound scanner with the scanning parameter set to a second value to provide a 3D ultrasound dataset that represents the tissue at the second time. A second volume rendering of 3D colorflow Doppler data associated with at least a portion of the tissue can be displayed based on the second 3D ultrasound dataset. Accordingly, volume renderings of the 3D colorflow Doppler data associated with the tissue may be provided in real time. Moreover, scanning parameters may be adjusted while the objects are being scanned.

DETAILED DESCRIPTION OF EMBODIMENTS OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Although embodiments according to the present invention are disclosed herein in reference to the scanning of tissue, it will be understood that the present invention may be utilized to scan other objects. For example, the present invention may be utilized to provide real time volume rendering of pipes. As used herein, the term "tissue" includes blood and organs, such as a heart, found in a biological body.

As used herein, the term "real time" is defined to include time intervals that may be perceived by a user as having little or substantially no delay associated therewith. For example, when a volume rendering using an acquired ultrasound dataset is described as being performed in real time, a time interval between acquiring the ultrasound dataset and displaying the volume rendering based thereon may be in a range of less than 1 second to reduce a time lag between an adjustment and a display that shows the adjustment. For example, some systems may typically operate with time intervals of about 0.10 seconds. Time intervals of more than one second may also be used.

It will be understood that the volume rendering disclosed herein can be gradient-based volume rendering that uses, for example, ambient, diffuse, and specular components of the 3D ultrasound data sets to render the volumes. Other components may also be used. It will also be understood that the volume renderings may include surfaces that are part of the exterior of an organ or are part of internal structures of the organ. For example, with regard to the heart, the volumes that are rendered can include exterior surfaces of the heart or interior surfaces of the heart where, for example, a catheter is guided through an artery to a chamber of the heart.

As will be appreciated by those of skill in the art, the present invention may be embodied as methods and/or systems. Accordingly, the present invention may take the form of hardware embodiments, software embodiments or embodiments that combine software and hardware aspects. Moreover, the components of ultrasound systems according to the present invention, including those described herein, may be packaged as a single unit or packaged separately and interconnected to provide embodiments of methods and systems according to the present invention.

The present invention is disclosed using flowchart and block diagram illustrations. It will be understood that blocks of the flowchart and block diagram illustrations, and combinations of blocks, can be implemented by computer program instructions. These program instructions may be provided to a processor circuit(s), such as a Digital Signal Processor (DSP) circuit, within an ultrasound system according to the present invention, such that the instructions which execute on the processor circuit(s) create means for implementing the functions specified in the block or blocks. The computer program instructions may be executed by the processor circuit(s) to cause a series of operational steps to be performed by the processor circuit(s) to produce a computer implemented process such that the instructions which execute on the processor circuit(s) provide steps for implementing the functions specified in the block or blocks.

Accordingly, the blocks support combinations of means for performing the specified functions, combinations of steps for performing the specified functions and program instructions for performing the specified functions. It will also be understood that each block, and combinations of blocks, can be implemented by special purpose hardware-based systems which perform the specified functions or steps, or combinations of special purpose hardware and computer instructions.

According to embodiments of methods and systems according to the present invention, an ultrasound scanner may display volume renderings of objects in real time. In particular, the system can scan an object to provide 3D ultrasound data for a display of a volume that is rendered to appear three dimensional on a two dimensional display. Moreover, the volume rendering may be provided in real time. Providing a display of a volume rendering in real time may provide for improved guidance of instruments used in procedures. Guidance may be improved, for example, by showing the anatomy under investigation in a more natural form so that a user may focus more on guiding the instrument and less on mentally visualizing the anatomy.

According to FIG. 1, an ultrasound scanner (or system), such as those described for example in U.S. Pat. No. 4,694,434 to von Ramm et al. (Von Ramm) entitled Three Dimensional Imaging System and U.S. Pat. No. 5,546,807 to Oxaal et al. (Oxaal) entitled High Speed volumetric Ultrasound Imaging System, the entire disclosures of which are incorporated herein by reference, can be used to scan a volume 100 using a transducer 115 to acquire 3D ultrasound datasets that represent an object (or objects) within the volume 100.

The 3D ultrasound dataset can include image data generated from echoes of ultrasound beams reflected from the object in the volume 100. Accordingly, the 3D ultrasound dataset can be a 'snapshot' of the object 105 in the volume 100 at a particular time. The object can be tissue, such as a heart 105, or other objects to be studied. A series of snapshots of the volume 100 can be acquired at a series of respective times. For example, the system may acquire one snapshot every 0.05 seconds over an entire cycle of a heart. The snapshots can be stored for later examination and/or viewed as they are acquired.

Figure 2:
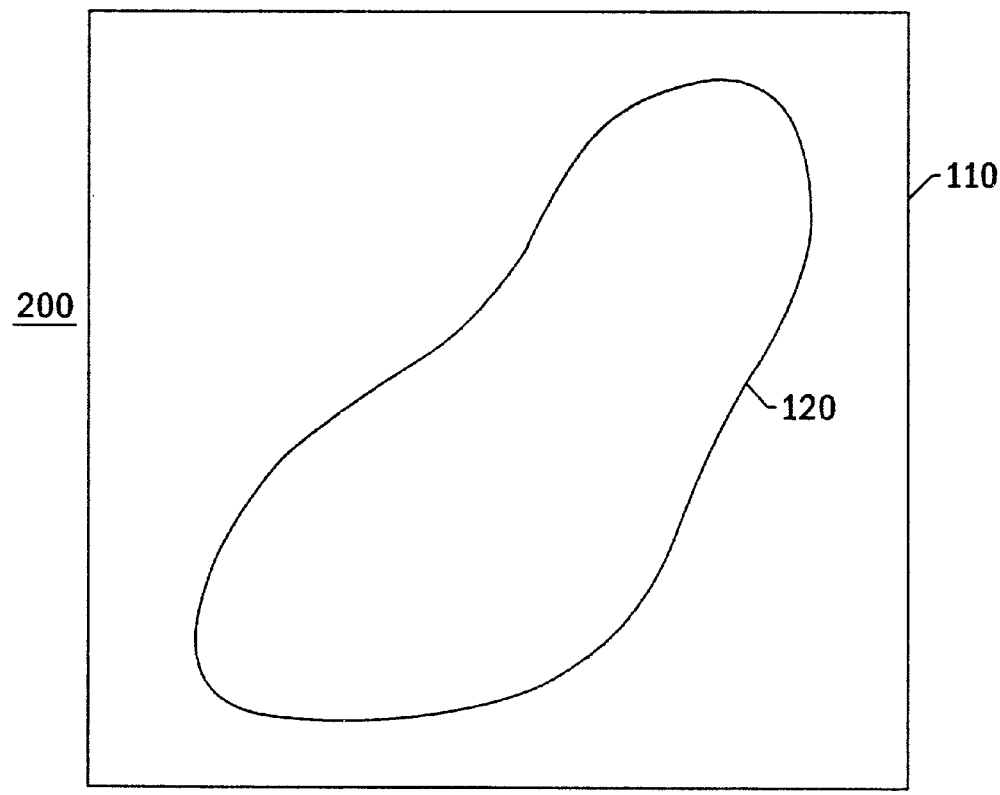
FIG. 2 is a schematic diagram of a view of a slice of an object in a scanned volume.

The ultrasound system may include means for displaying views of the acquired image data included in the 3D ultrasound dataset. The views can be of 'slices' of the tissue in volume 100. For example, the system can provide a view 200 of a slice 110 that passes through the heart 105 as indicated by the area 120 shown in FIG. 1. FIG. 2 shows such a view 200 of the slice 110. The view 200 can include image data that corresponds to the area 120 where the slice 110 intersects the heart 105 (see FIG. 1). The system can provide the view 200 by selecting image data from the 3D ultrasound dataset that lies on or within the slice 110 as disclosed in Oxaal.

It will be understood that the slice 110 can be an Inclined (I) slice, a Constant depth (C) slice, a B-mode slice, or any other type of cross-section of the tissue at any orientation. For example, the slice 110 can be inclined or 'tilted' at an arbitrary angle within the volume 100.

Figure 3:
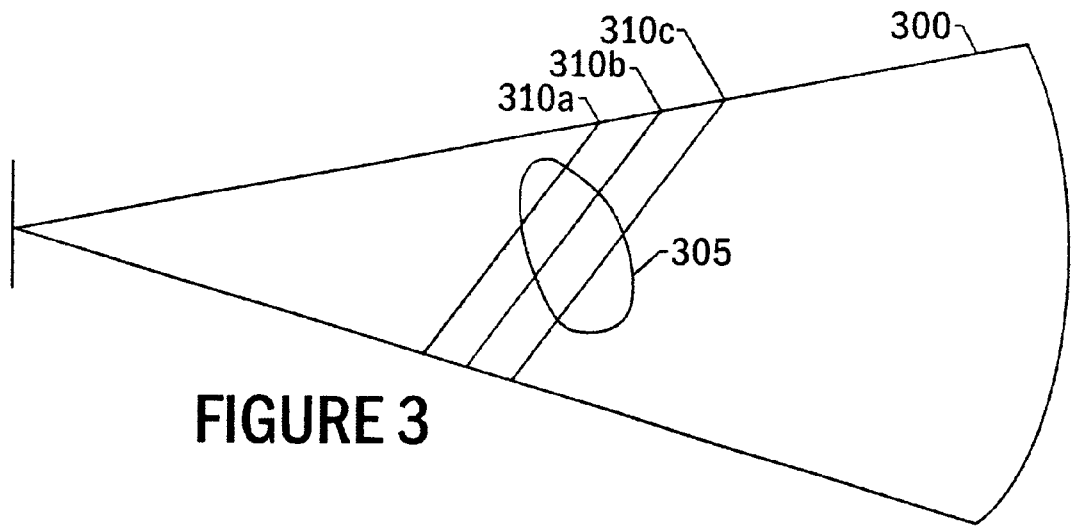
FIG. 3 is a schematic diagram of a side view of slices of an object in a scanned volume.

As shown in FIG. 3, different slices 310a–c can be selected for display. For example, a user may select the slices 310a–c of the image data from the 3D ultrasound dataset that correspond to the different depths of an object 305. As disclosed in Oxaal, the system may need to scan the volume 300 only one time to acquire the 3D ultrasound dataset. Thereafter, the system can provide the views of the different slices 310a–c by selecting the image data that corresponds to the slices 310a–c without requiring any further scans.

Figure 4:
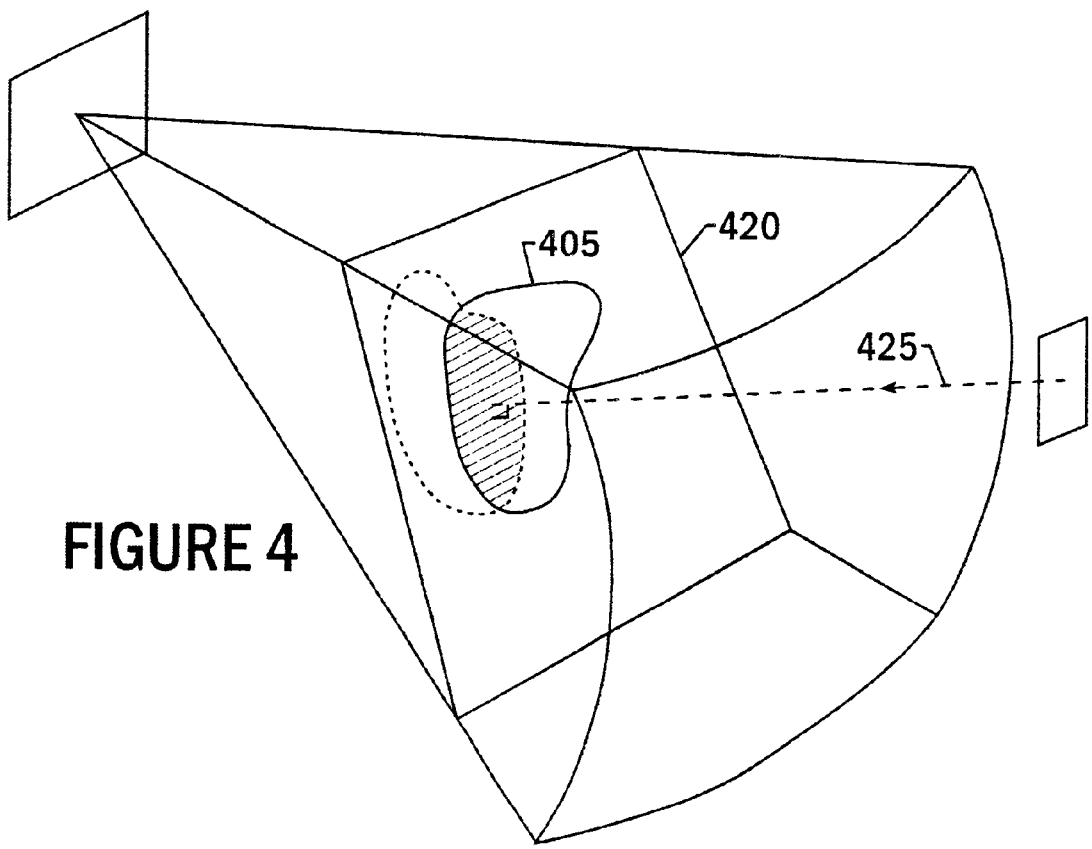
FIG. 4 is a schematic diagram that illustrate embodiments of methods and systems according to the present invention that define slices of objects to be rendered based on viewing directions.
Figure 5:
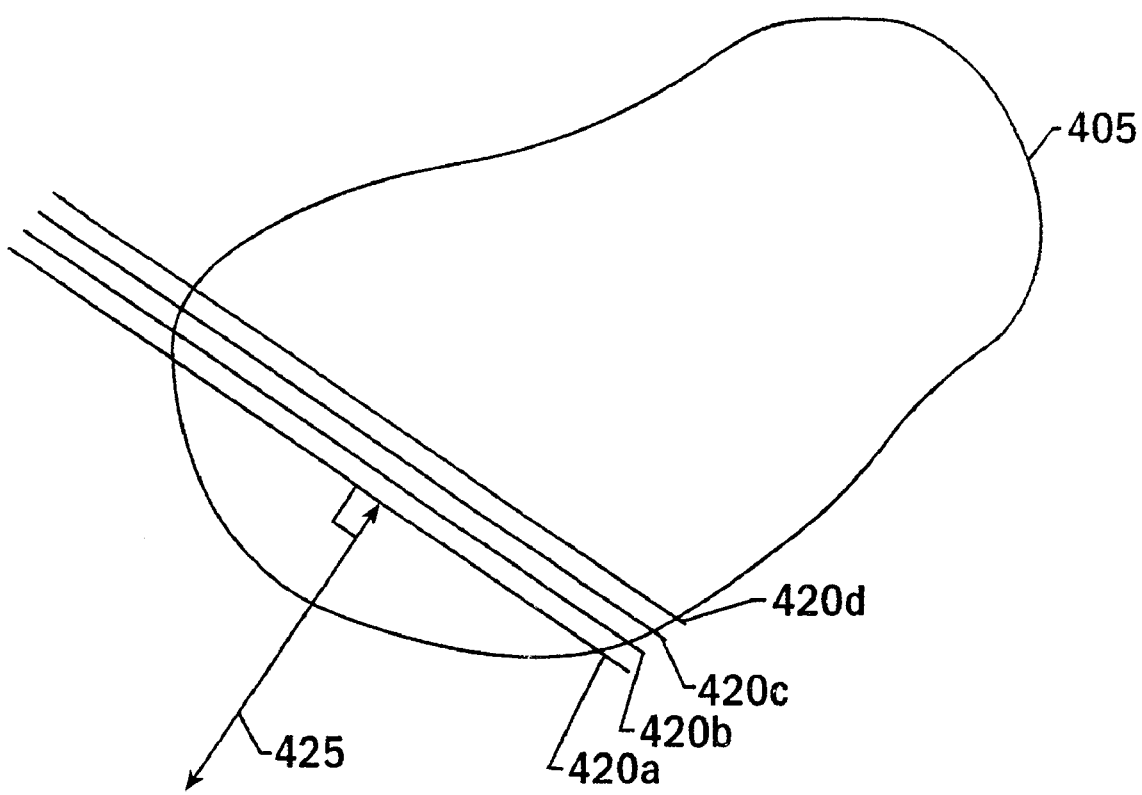
FIG. 5 is a schematic diagram that illustrate embodiments of methods and systems according to the present invention that define slices of objects to be rendered based on viewing directions.

As shown in FIG. 4, a slice 420 can be orthogonal to a viewing direction 425. For example, if a user specifies the viewing direction 425 for display of a volume rendering of an object 405, the slice 420 of the 3D ultrasound dataset is selected so as to be orthogonal to the viewing direction 425. Moreover, a plurality of orthogonal slices 420a–d of the 3D ultrasound dataset can be used to provide a volume rendering of the object 405 as shown, for example, in FIG. 5. In other embodiments according to the present invention, the slices may define an arbitrary angle with the viewing direction, as disclosed, for example, in Oxaal.

Figures 6, 7:
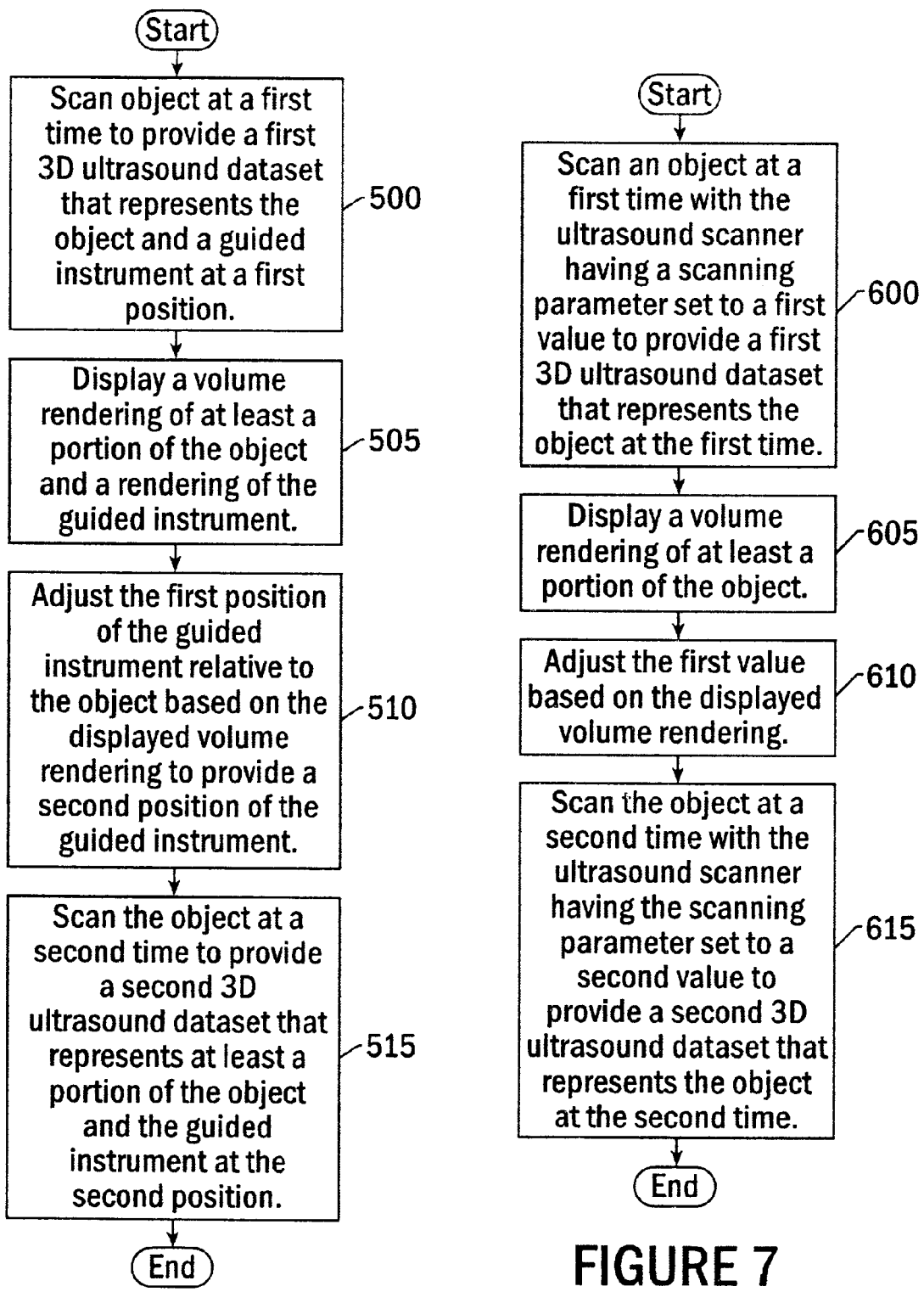
FIG. 6 is a flowchart that illustrates embodiments of methods and systems according to the present invention.
FIG. 7 is a flowchart that illustrates embodiments of methods and systems according to the present invention.

FIG. 6 is a flowchart that illustrates embodiments of methods and systems according to the present invention. In particular, an object can be scanned at a first time using the ultrasound scanner to provide a first 3D ultrasound dataset that represents the object and an instrument at a first position (block 500). A volume rendering of at least a portion of the object and a rendering of the instrument can be displayed (block 505). The first position of the instrument can be adjusted relative to the object based on the displayed volume rendering to provide a second position of the instrument (block 510). The object is scanned at a second time using the ultrasound scanner to provide a second 3D ultrasound dataset that represents at least a portion of the object and the instrument at the second position (block 515).

The adjusted position of the instrument may be seen in a display of a volume rendering of the object and the instrument using the second 3D ultrasound dataset. Moreover, the instrument can be continually guided by repeatedly scanning and displaying the volume renderings of the object and the instrument as the instrument is manipulated. For example, in some embodiments, the instrument can be a catheter used, for example, during examinations of the heart. In such procedures, the instrument may be guided to the heart by reference to displayed volume rendered surfaces.

In other embodiments, the instrument can be a biopsy needle used to sample and remove tissue for analysis. In such embodiments, the instrument may be guided to the tissue to be sampled by referring to the volume renderings of the tissue. Embodiments according to the present invention may, therefore, enable more accurate tissue biopsies. In other embodiments, the instrument can be an amniocentesis needle used to sample amniotic fluid in fetus investigations. A volume rendering of the fetus may thereby reduce the risk that the needle injures the fetus.

Moreover, the volume rendering can be displayed as a transducer is moved. For example, if the transducer is moved between the first and second scans, a display of the volume rendering can be based on the new location of the transducer. Accordingly, the displayed volume renderings may provide a more natural display to the user. In contrast, conventional systems may not allow real time display of volume renderings because all of the scanning may be completed prior to rendering the volume.

FIG. 7 is a flowchart that illustrates embodiments of methods and systems according to the present invention. In particular, ultrasound images can be generated using an ultrasound scanner by scanning an object at a first time with the ultrasound scanner where a scanning parameter is set to a first value to provide a first 3D ultrasound dataset that represents the object at the first time (block 600). A volume rendering of at least a portion of the object can be displayed (block 605). The first value can be adjusted based on a view that is generated from the first 3D ultrasound dataset (block 610). The object can be scanned at a second time with the ultrasound scanner where the scanning parameter is set to a second value to provide a second 3D ultrasound dataset that represents the object at the second time (block 615).

Accordingly, the value of the scanning parameter can be adjusted as the object is being scanned by the ultrasound scanner. For example in some embodiments, the scanning parameter can be a position of a transducer used to scan the object. In other embodiments, the scanning parameter can be a scanning gain that can affect the signals that are used to scan the object. In still other embodiments, the scanning parameter can be a depth of scanning that can control how the object is scanned.

Figure 8:
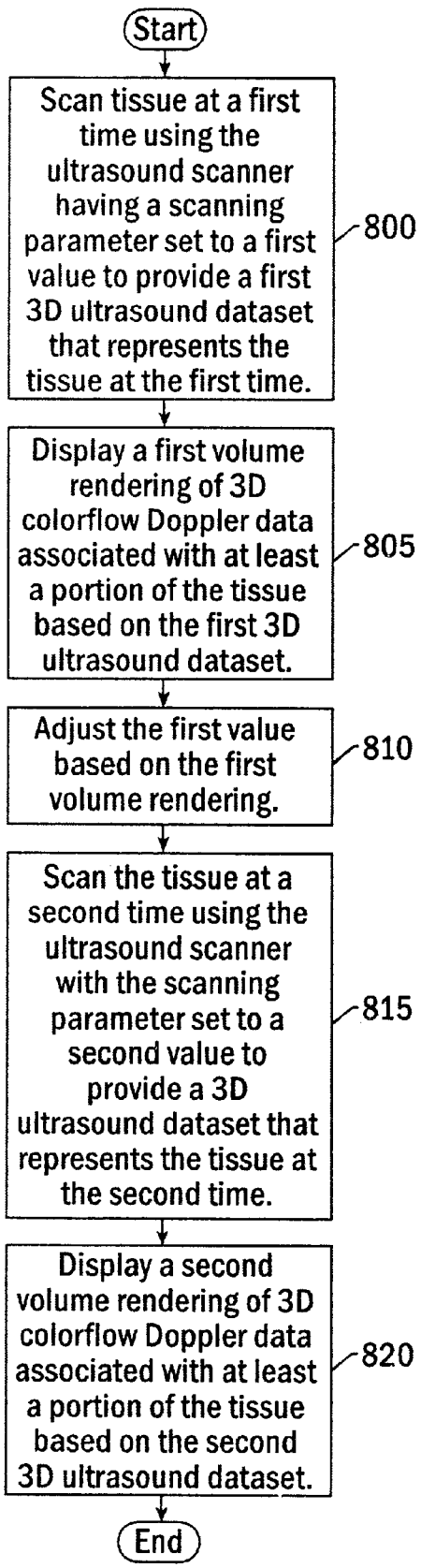
FIG. 8 is a flowchart that illustrates embodiments of methods and systems according to the present invention.

FIG. 8 is a flowchart that illustrates embodiments of methods and systems according to the present invention. In particular, colorflow Doppler ultrasound images can be provided by scanning tissue at a first time using the ultrasound scanner having a scanning parameter set to a first value to provide a first 3D ultrasound dataset that represents the tissue at the first time (block 800). A first volume rendering of 3D colorflow Doppler data associated with at least a portion of the tissue can be displayed based on the first 3D ultrasound dataset (block 805). The first value can be adjusted based on the first volume rendering (block 810). The tissue can be scanned at a second time using the ultrasound scanner with the scanning para meter set to a second value to provide a 3D ultrasound dataset that represents the tissue at the second time (block 815). A second volume rendering of 3D colorflow Doppler data associated with at least a portion of the tissue can be displayed based on the second 3D ultrasound dataset (block 820). Accordingly, volume renderings of the 3D colorflow Doppler data associated with the tissue may be provided in real time.

Figure 12:
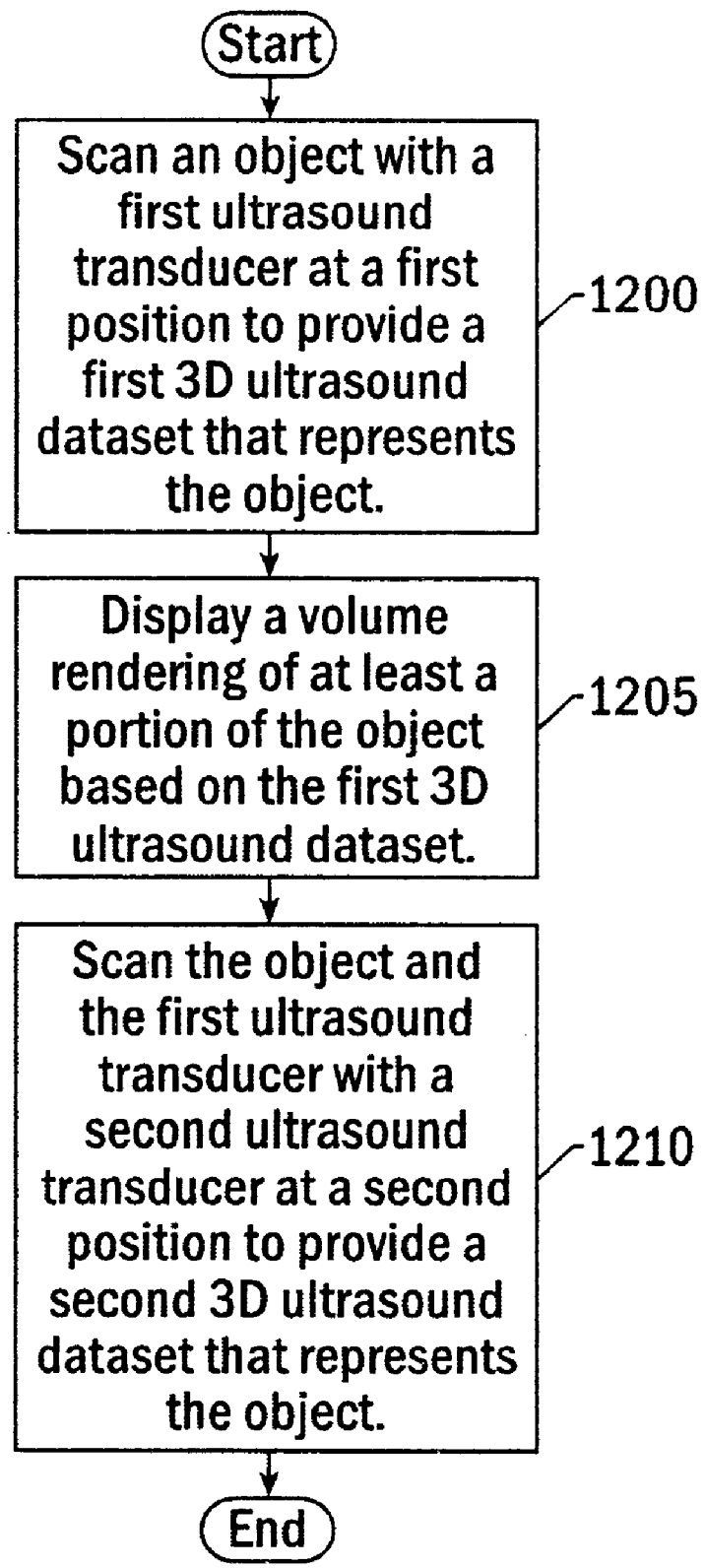
FIG. 12 is a flowchart that illustrates embodiments of methods and systems according to the present invention.

FIG. 12 is a schematic diagram that illustrates embodiments of methods and systems according to the present invention. In particular, embodiments of methods and systems for real time volume rendering of ultrasound data according to the present invention may be provided by scanning an object with a first ultrasound transducer at a first position to provide a first 3D ultrasound dataset that represents the object (block 1200). A volume rendering of at least a portion of the object can be displayed based on the first 3D ultrasound dataset (block 1205). The object and the first ultrasound transducer can be scanned with a second ultrasound transducer at a second position to provide a second 3D ultrasound dataset that represents the first transducer relative to the object (block 1210).

Figure 13:
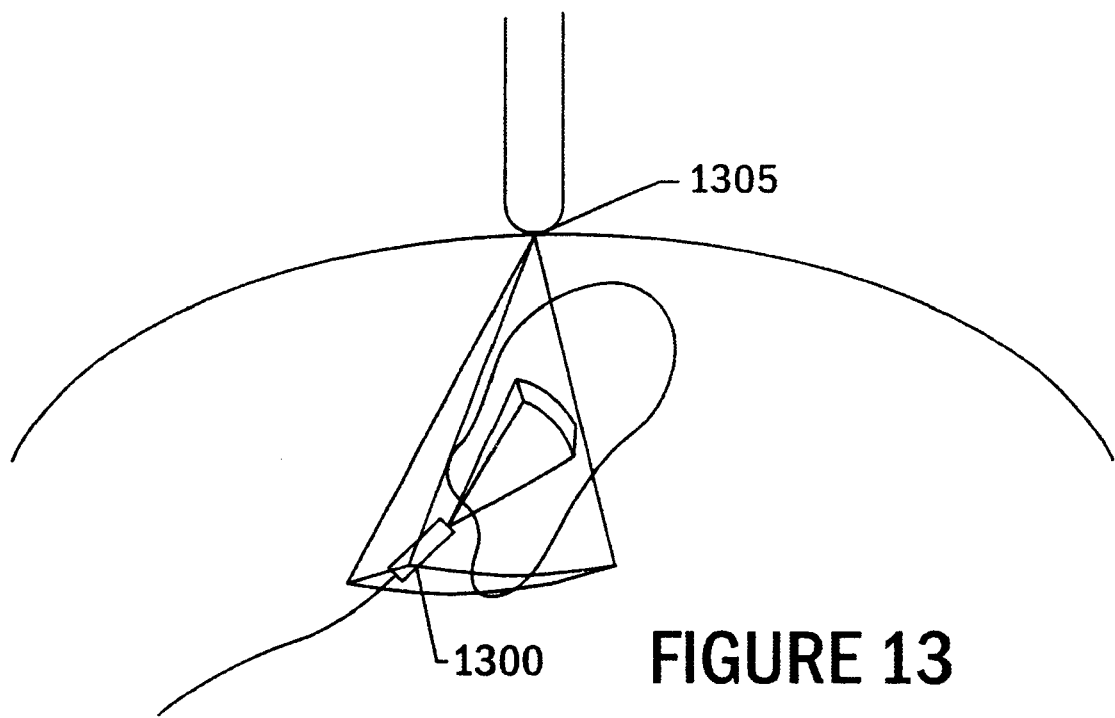
FIG. 13 is a schematic diagram that illustrates embodiments of methods and systems according to the present invention.

Accordingly, a volume rendering of the first ultrasound transducer in the first position 1300 relative to the object may be provided from the perspective of the second position 1305, as shown for example in FIG. 13. In one embodiment according to the present invention, the first ultrasound transducer can be attached to a catheter so that a volume rendering of the object may be provided. The second 3D ultrasound dataset may provide a basis for a rendering that includes the first ultrasound transducer which may be used to provide for display of the first position 1300 of the first ultrasound transducer relative to the object. In some embodiments, the second ultrasound transducer can be located outside a body that contains the object to which the volume rendering corresponds. In other embodiments, the first and second 3D ultrasound datasets can be used to provide first and second volume renderings from the perspectives of the first and second positions. In still other embodiments, the first and second 3D ultrasound datasets can be combined to provide a combined volume rendering.

Figure 9:
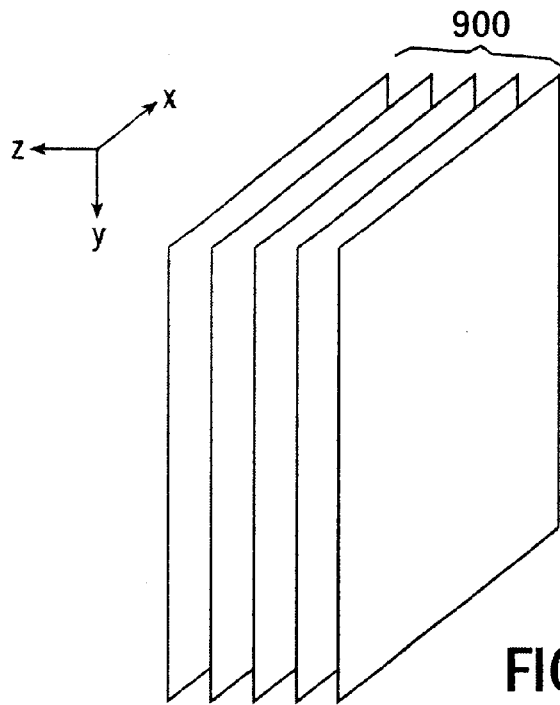
FIG. 9 is a schematic diagram of a series of 2D rectangular slices of a volume according to embodiments of the present invention.
Figure 10:
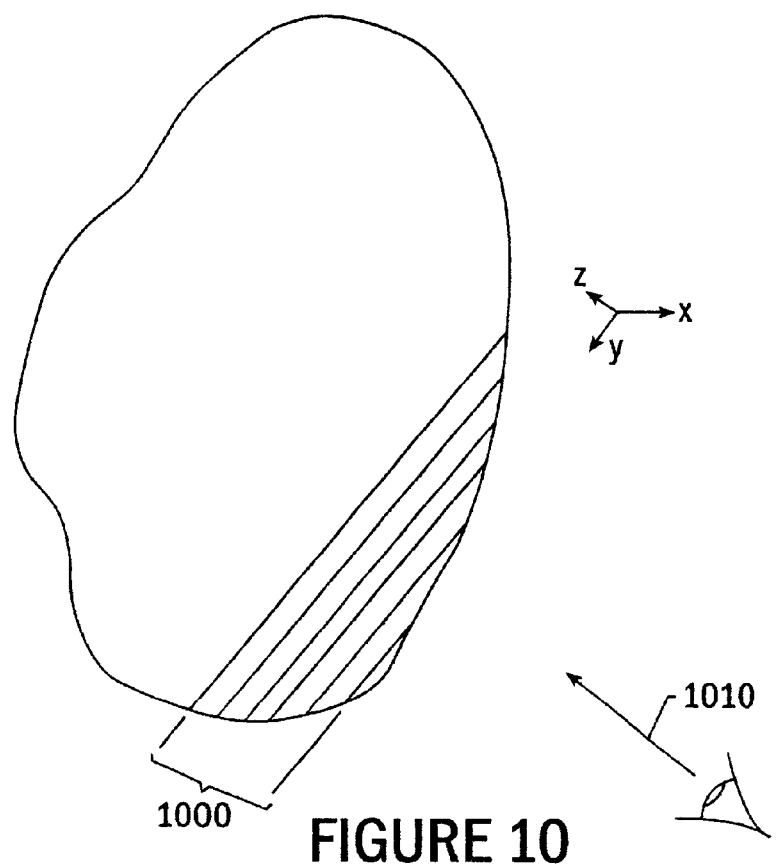
FIG. 10 is a schematic diagram of a series of 2D rectangular orthogonal slices of a volume from a viewing direction and viewing angle according to embodiments of the present invention.
Figure 11:
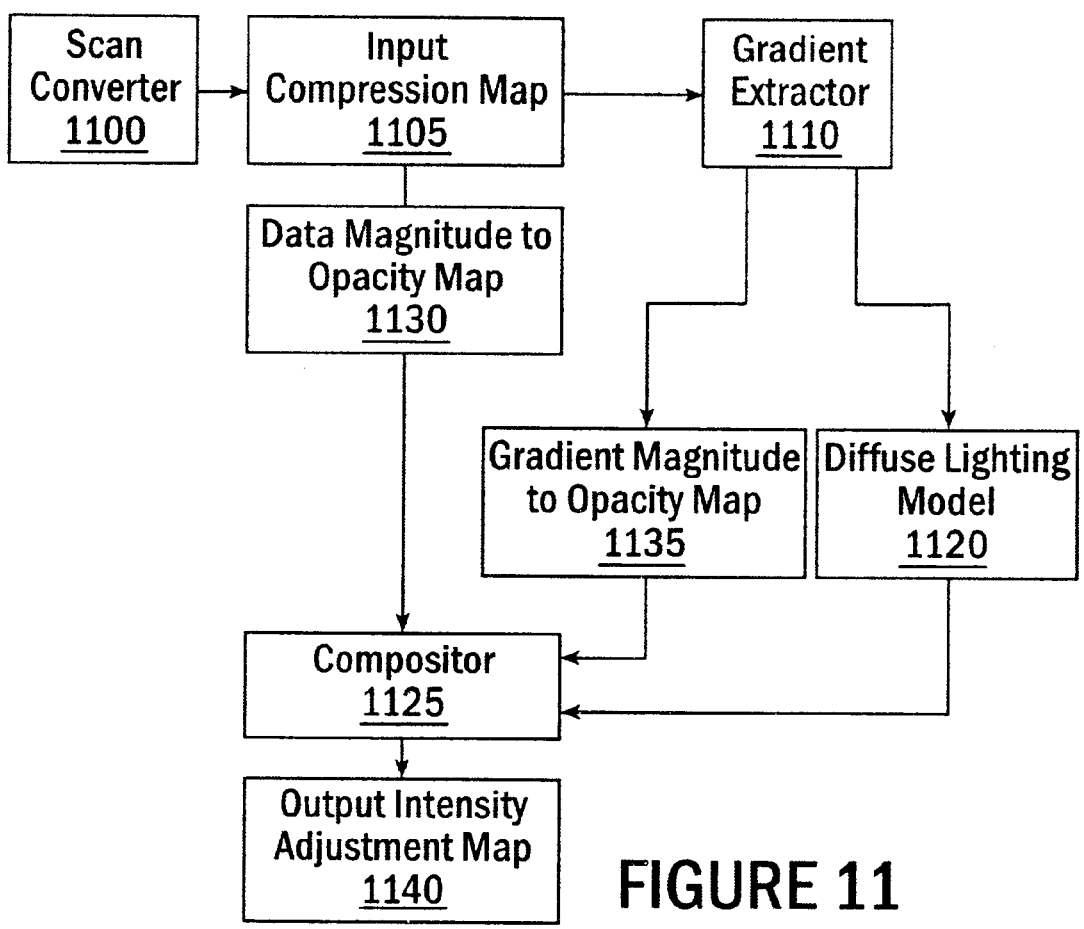
FIG. 11 is a block diagram that illustrates embodiments of methods and systems according to the present invention.

Volume rendering according to the present invention will now be described in further detail in reference to FIG. 11. According to embodiments of the present invention, a scan converter 1100, such as that disclosed in Oxaal, can produce a series of 2D rectangular slices 900 of the volume that samples, or voxels, that, for example, have the same extent but steadily decreasing depths, as shown in FIG. 9. The number of slices in the stack, as well as the overall change in depth from back to front, maybe adjusted in real time. As shown in FIG. 10, the slices 1000 can be oriented orthogonally to a viewing angle 1010 that is associated with the view of the volume rendering that is being generated.

The slices can be passed through a compression map 1105 which can compensate for voxels having low intensity values. The compensated slices can be passed through a gradient extractor 1110 which can determine a 3-D gradient vector at each voxel by comparing the intensity values of neighboring voxels. By negating and normalizing the gradient vector, a surface normal vector 1115 can be produced. The normal vector 1115 can be used for shading the data using a diffuse lighting model 1120. The lighting model 1120 can be expressed as:

$$D_{OUT}=(K_A+K_Z(N \cdot L))^*D_{IN} \quad (1)$$

where $K_A$ is the ambient light contribution constant, $K_Z$ is the depth intensity rolloff factor (which is a function of the number of slices that have been processed), L is the lighting vector, and N is the normal vector.

A shaded slice can be composited by a compositor 1125 with the slices of greater depth that have been already been processed. The compositing can be accomplished by linear interpolation, as expressed by:

$$D_{OUT}=(\text{Opacity}^*D_{PRESENT})+((1-\text{Opacity})^*D_{PAST}) \quad (2)$$

to provide a composited slice.

An opacity factor can be determined by multiplying the output of two different maps: a Data Magnitude—to—Opacity map 1130 and a Gradient Magnitude—to—Opacity map 1135. These two maps can provide voxel classification. Accordingly, voxels with desirable values and/or local gradients may be opaque in the volume rendering. Moreover, undesirable data may be suppressed by, for example, tending to make the undesirable voxels more transparent and, therefore, less noticeable.

The composited slice can be passed through the output intensity adjustment map 1140 to brighten the volume rendering. This can compensate for mathematical losses that can accumulate when compositing the slices. The brightened image can be displayed as a volume rendering according embodiments of the present invention.

In the drawings and specification, there have been disclosed typical preferred embodiments of the invention and, although specific tenns are employed, they are used in a generic and descriptive sense only and not for purposes of limitation, the scope of the invention being set forth in the following claims. Analogous system and computer program product claims may be provided.

What is claimed:

1. A method for real time volume rendering of ultrasound data using 2D ultrasound transducer array, the method comprising:
    scanning an object with a first 2D ultrasound transducer array at a first position to provide a first 3D ultrasound dataset that represents the object;
    displaying a first volume rendering of at least a portion of the object based on the first 3D ultrasound dataset; and
    scanning the object and the first 2D ultrasound transducer array using a second 2D ultrasound transducer array at a second position to provide a second 3D ultrasound dataset used to display a second volume rendering that represents the object and the first 2D ultrasound transducer array.

2. A method according to claim 1, wherein the scanning of the first and second 2D ultrasound transducer arrays is interleaved.

3. A method according to claim 1 further comprising:
    displaying a rendering of at least a portion of the object and the first 2D ultrasound transducer array based on the second 3D ultrasound dataset.

4. A method according to claim 3, wherein the rendering is a volume rendering.

5. A method according to claim 1, wherein at least one of the first and second volume renderings comprises colorflow Doppler ultrasound data.

6. A method according to claim 1 further comprising:
    guiding an instrument based on at least one of the first and second volume renderings.

7. A method according to claim 6 wherein the instrument is selected from a list consisting of a biopsy needle, a catheter, and an amniocentesis needle.

8. A method according to claim 1 further comprising:
    adjusting a position of at least one of the first and second ultrasound transducer arrays.

9. A method according to claim 1 further comprising:
    treating the object with a contrast agent.

10. A system for real time volume rendering of ultrasound data using 2D ultrasound transducer array, the system comprising:
    means for scanning an object with a first 2D ultrasound transducer array at a first position to provide a first 3D ultrasound dataset that represents the object;
    means for displaying a first volume rendering of at least a portion of the object based on the first 3D ultrasound dataset; and
    means for scanning the object and the first 2D ultrasound transducer array using a second 2D ultrasound transducer array at a second position to provide a second 3D ultrasound dataset used to display a second volume rendering that represents the object and the first 2D ultrasound transducer array.

11. A system according to claim 10, wherein the means for scanning interleaves scanning of the first and second 2D ultrasound transducer arrays.

12. A system according to claim 10 further comprising:
    means for displaying a rendering of at least a portion of the object and the first 2D ultrasound transducer array based on the second 3D ultrasound dataset.

* * * * *

UNITED STATES PATENT AND TRADEMARK OFFICE
CERTIFICATE OF CORRECTION

| | |
|---|---|
| PATENT NO. | : 6,544,178 B1 |
| APPLICATION NO. | : 09/707241 |
| DATED | : April 8, 2003 |
| INVENTOR(S) | : Grenon et al. |

It is certified that error appears in the above-identified patent and that said Letters Patent is hereby corrected as shown below:

On the title page item (75), should include the following inventors:

Stephen W. Smith, Durham, NC (US); Edward D. Light, Durham, NC (US)

Signed and Sealed this

Tenth Day of October, 2006

JON W. DUDAS
*Director of the United States Patent and Trademark Office*